(12) United States Patent  (10) Patent No.: US 8,216,259 B2
Gurtner et al.  (45) Date of Patent: Jul. 10, 2012

(54) COMPOSITIONS AND METHODS FOR JOINING NON-CONJOINED LUMENS

(75) Inventors: Geoffrey C. Gurtner, Stanford, CA (US); Gerald G. Fuller, Stanford, CA (US); Michael T. Longaker, Atherton, CA (US); Jayakumar Rajadas, Stanford, CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 1225 days.

(21) Appl. No.: 11/766,779

(22) Filed: Jun. 21, 2007

(65) Prior Publication Data

US 2008/0045985 A1  Feb. 21, 2008

Related U.S. Application Data

(60) Provisional application No. 60/805,425, filed on Jun. 21, 2006, provisional application No. 60/806,242, filed on Jun. 29, 2006, provisional application No. 60/914,635, filed on Apr. 27, 2007.

(51) Int. Cl.
*A61B 17/08* (2006.01)
(52) U.S. Cl. .................................. 606/153; 606/154
(58) Field of Classification Search .............. 606/153, 606/214–215, 154
See application file for complete search history.

(56) References Cited

U.S. PATENT DOCUMENTS

| | | | |
|---|---|---|---|
| 3,321,276 A | | 5/1967 | Burzynski et al. |
| 3,683,926 A | * | 8/1972 | Suzuki ........................... 606/154 |
| 3,740,421 A | | 6/1973 | Schmolka et al. |
| 4,035,334 A | * | 7/1977 | Davydov et al. ........... 424/78.06 |
| 4,657,019 A | | 4/1987 | Walsh et al. |
| 4,770,176 A | | 9/1988 | McGreevy et al. |
| 5,141,516 A | | 8/1992 | Detweiler |
| 5,143,731 A | | 9/1992 | Viegas et al. |
| 5,180,392 A | * | 1/1993 | Skeie et al. ................. 623/23.64 |
| 5,183,879 A | | 2/1993 | Yuasa et al. |
| 5,366,735 A | | 11/1994 | Henry |
| 5,469,867 A | * | 11/1995 | Schmitt ......................... 128/898 |
| 5,525,334 A | | 6/1996 | Ito et al. |
| 5,534,186 A | | 7/1996 | Walker et al. |
| 5,565,139 A | | 10/1996 | Walker et al. |
| 5,589,568 A | | 12/1996 | Higashijima et al. |
| 5,643,246 A | | 7/1997 | Leeb et al. |

(Continued)

FOREIGN PATENT DOCUMENTS

CN 1377706 5/2007

(Continued)

OTHER PUBLICATIONS

S. Beltran, J. P. Baker, H. H. Hooper, H. W. Blanch and J. M. Prausnitz, "Swelling Equilibria for Weakly Ionizable, Temperature-Sensitive Hydrogels", *Macromolecules*, vol. 24, No. 2, 549-551 (1991).

(Continued)

*Primary Examiner* — Corrine M McDermott
*Assistant Examiner* — Gregory Anderson
(74) *Attorney, Agent, or Firm* — Foley & Lardner LLP

(57) ABSTRACT

Disclosed are compositions, methods, and kits for joining together non-conjoined lumens in a patient's body including vascular lumens. More particularly, in various aspects, this invention provides compositions, methods, and kits for joining such non-conjoined lumens, including small lumens typically requiring microsurgical technique.

42 Claims, 5 Drawing Sheets

U.S. PATENT DOCUMENTS

| | | | |
|---|---|---|---|
| 5,651,979 | A | 7/1997 | Ron et al. |
| 5,653,744 | A | 8/1997 | Khouri |
| 5,681,576 | A | 10/1997 | Henry |
| 5,695,480 | A | 12/1997 | Evans et al. |
| 5,702,361 | A | 12/1997 | Evans et al. |
| 5,702,717 | A | 12/1997 | Cha et al. |
| 5,726,456 | A | 3/1998 | Lupton et al. |
| 5,787,900 | A | 8/1998 | Butler et al. |
| 5,834,007 | A | 11/1998 | Kubota |
| 5,858,746 | A | 1/1999 | Hubbell et al. |
| 5,861,174 | A | 1/1999 | Stratton et al. |
| 6,004,573 | A | 12/1999 | Rathi et al. |
| 6,018,033 | A | 1/2000 | Chen et al. |
| 6,201,065 | B1 | 3/2001 | Pathak et al. |
| 6,309,663 | B1 | 10/2001 | Patel et al. |
| 6,413,537 | B1 | 7/2002 | Kwon et al. |
| 6,488,954 | B1 | 12/2002 | Yoon et al. |
| 6,562,362 | B1 | 5/2003 | Bae et al. |
| 6,660,247 | B1 | 12/2003 | Gutowska et al. |
| 6,743,436 | B1 | 6/2004 | Lee et al. |
| RE38,558 | E | 7/2004 | Emanuele et al. |
| 6,761,824 | B2 | 7/2004 | Reeve et al. |
| 6,761,903 | B2 | 7/2004 | Chen et al. |
| 6,897,064 | B2 | 5/2005 | Yoshioka et al. |
| 6,923,986 | B2 | 8/2005 | Pathak et al. |
| 6,939,364 | B1 | 9/2005 | Soltz et al. |
| 6,977,045 | B2 | 12/2005 | Reeve et al. |
| 6,991,804 | B2 | 1/2006 | Helmus et al. |
| 7,011,677 | B2 | 3/2006 | Wallace et al. |
| 7,018,645 | B1 | 3/2006 | Piao et al. |
| 7,033,571 | B2 | 4/2006 | Gutowska et al. |
| 7,044,982 | B2 | 5/2006 | Milbocker |
| 7,083,806 | B2 | 8/2006 | Rippon et al. |
| 7,160,931 | B2 | 1/2007 | Cheng et al. |
| 7,169,404 | B2 | 1/2007 | Hossainy et al. |
| 7,193,007 | B2 | 3/2007 | Cheng et al. |
| 7,641,643 | B2 | 1/2010 | Michael et al. |
| 7,691,140 | B2 * | 4/2010 | Bates et al. .......... 623/1.13 |
| 2003/0100920 | A1 * | 5/2003 | Akin et al. .......... 606/213 |
| 2003/0191209 | A1 | 10/2003 | Guan et al. |
| 2004/0096508 | A1 | 5/2004 | Gutowska et al. |
| 2004/0213756 | A1 | 10/2004 | Michael et al. |
| 2004/0220283 | A1 | 11/2004 | Zhang et al. |
| 2004/0253277 | A1 | 12/2004 | Meadows et al. |
| 2004/0266983 | A1 | 12/2004 | Reeve et al. |
| 2005/0008610 | A1 | 1/2005 | Schwarz et al. |
| 2005/0027019 | A1 | 2/2005 | Zhang et al. |
| 2005/0079147 | A1 | 4/2005 | Delaey et al. |
| 2005/0143678 | A1 | 6/2005 | Schwarz et al. |
| 2005/0147585 | A1 | 7/2005 | Schwarz et al. |
| 2005/0181062 | A1 | 8/2005 | Appel et al. |
| 2005/0220881 | A1 | 10/2005 | Mehta et al. |
| 2006/0078616 | A1 | 4/2006 | Georgewill et al. |
| 2006/0269512 | A1 | 11/2006 | McDougal et al. |
| 2007/0202177 | A1 | 8/2007 | Hoang |
| 2007/0237740 | A1 | 10/2007 | Reddington et al. |
| 2008/0031847 | A1 | 2/2008 | Cohn |
| 2008/0181952 | A1 | 7/2008 | Vogel et al. |
| 2008/0208163 | A1 | 8/2008 | Wilkie |
| 2008/0215036 | A1 | 9/2008 | Vogel et al. |
| 2008/0262519 | A1 | 10/2008 | Gurtner et al. |
| 2009/0162438 | A1 | 6/2009 | Fuller et al. |
| 2009/0187199 | A1 | 7/2009 | Gurtner et al. |

FOREIGN PATENT DOCUMENTS

| | | |
|---|---|---|
| EP | 0 386 960 | 9/1990 |
| EP | 0 327 325 | 10/1996 |
| EP | 1 266 570 | 12/2002 |
| EP | 0 724 888 | 5/2003 |
| EP | 1 407 791 | 4/2004 |
| KR | 20040028336 | 4/2004 |
| WO | WO 96/33673 | 10/1996 |
| WO | WO-96/33673 | 10/1996 |
| WO | WO-02/14380 | 2/2002 |
| WO | WO-2004/084703 | 10/2004 |
| WO | WO-2005/037062 | 4/2005 |
| WO | WO-2005/046438 | 5/2005 |
| WO | WO-2005/100441 | 10/2005 |
| WO | WO-2006/119009 | 11/2006 |
| WO | WO 2007/149999 | 12/2007 |
| WO | WO-2008/018892 | 2/2008 |
| WO | WO-2008/033728 | 3/2008 |
| WO | WO 2008/073938 | 6/2008 |
| WO | WO-2008/103891 | 8/2008 |
| WO | WO 2009/086206 | 7/2009 |
| WO | WO 2009/086207 | 7/2009 |
| WO | PCT/US2010/023155 | 2/2010 |

OTHER PUBLICATIONS

G. Chen and A. S. Hoffman, "Graft Copolymers That Exhibit Temperature-induced Phase Transitions Over a Wide Range of pH", *Nature*, vol. 373: 49-52 (1995).

Dumortier et al., "A Review of Polexamer 407 Pharmaceutical and Pharmacological Characteristics" *Pharmaceutical Research*, vol. 23, No. 12, pp. 2709-2728 (2006).

P.C. Leung, et al., "Biodegradable, Thermosensitive Implant for Approximating Cylindrical Structures: A Preliminary Study", *Microsurgery* 23:123-129 (2003).

T. G. Park, "Temperature Modulated Protein Release From pH/Temperature Sensitive Hydrogels" *Biomaterials* 20: 517-521 (1999).

T. G. Park and A. S. Hoffman, "Synthesis, Characterization, and Application of pH/Temperature-Sensitive Hydrogels", *Proceed. Intern. Symp. Control. Rel. Bioact. Mater.*, 17: 112-113 (1990).

Steedman, H.F., "A New Ribboning Embedding Medium for Histology", *Nature* 179:1345 (1957).

J. Zhang and N. A. Peppas, "Synthesis and Characterization of pH—and Temperature-Sensitive Poly(Methacrylic acid)/Poly(N isopropylacrylamide) Interpenetrating Polymeric Networks" *Macromolecules* (2000), 33: 102-107.

U.S. Appl. No. 12/367,201, filed Feb. 6, 2009, C. Travis Rappleye et al.

Escobar-Chavez et al., "Applications of Thermo-Reversible Pluronic F-128 Gels in Pharmaceutical Formulations," J. Pharm Pharmaceut. Sci. (www.csps Canada.org), vol. 9, No. 3, pp. 339-358 (2006).

Kamiji, T. et al., "Microvascular anastomosis using polyethylene glycol 4000 and fibrin glue," British Journal of Plastic Surgery, 1989, vol. 42, pp. 54-58.

Cong, Z et al., "Experimental Study on Microvascular Anastomosis Using a Dissolvable Stent Support in the Lumen", Microsurgery, 1991, vol. 12, pp. 67-71.

Kania, N. M. et al., "A new method of microvascular anastomosis: Clips with a soluble stent", 1998, pp. 245-248. (English abstract provided).

Moskovitz, M., "Microvascular Anastomoses Utilitzing New Intravascular Stents", 1994, vol. 32, pp. 612-618.

Nakata, S. et al., "End-to-side and end-to-end vascular anastomoses with a carbon dioxide laser", The Journal of Thoracic and Cardiovascular Surgery, 1989, vol. 98, pp. 1-2.

Bavbek, T. et al., "Problems with Attempted Chorioretinal Venous anastomosis by Laswer for Nonischemic CRVO and BRVO", 2005, vol. 219, No. 5, pp. 1-2.

International Search Report dated Jul. 25, 2008.

* cited by examiner

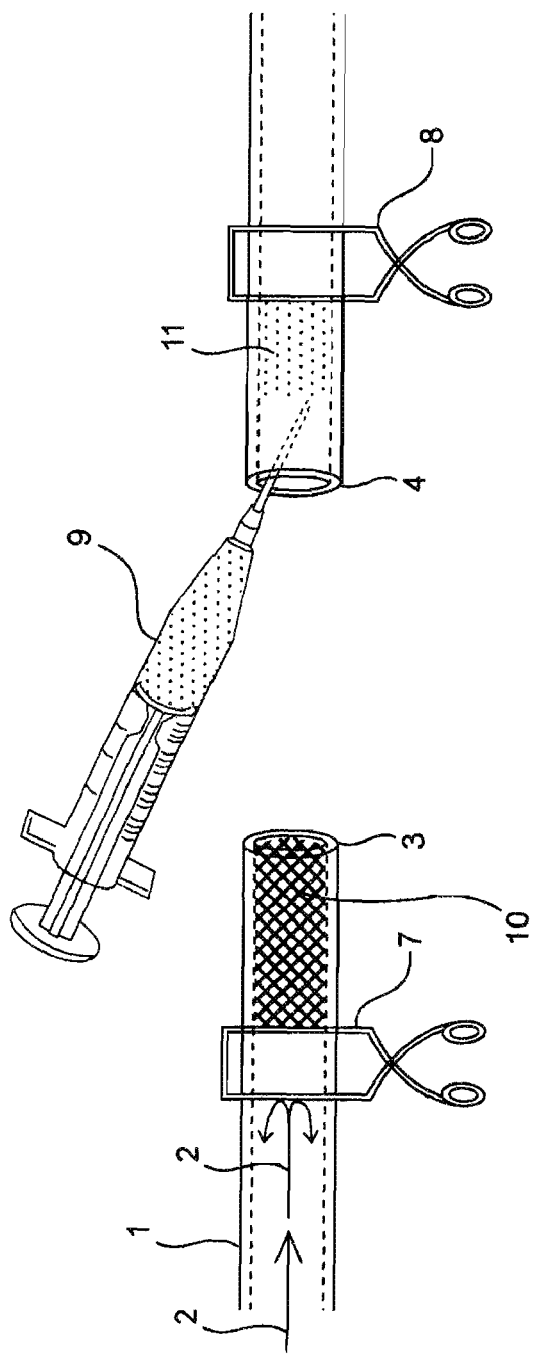
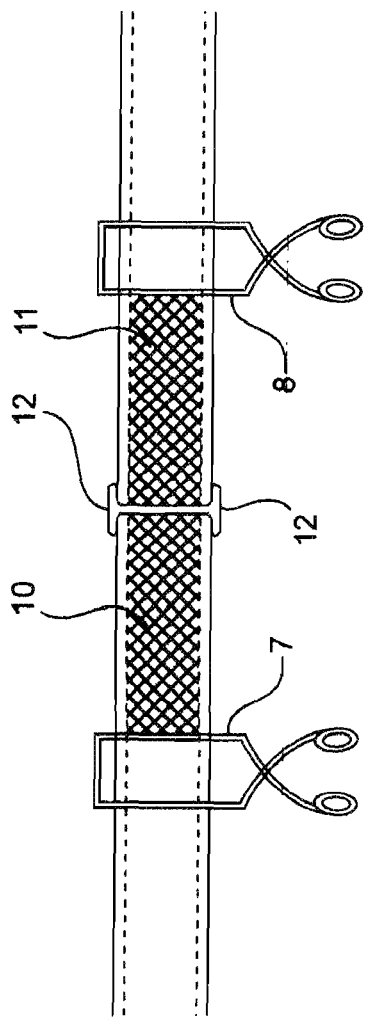
FIG. 3
FIG. 4

COMPOSITIONS AND METHODS FOR JOINING NON-CONJOINED LUMENS

CROSS-REFERENCE TO RELATED APPLICATIONS

This application claims the benefit under 35 U.S.C. § 119 (e) of provisional Patent Application Ser. Nos. 60/805,425, filed on Jun. 21, 2006, 60/806,242, filed on Jun. 29, 2006, and 60/914,635, filed on Apr. 27, 2007, all of which are incorporated herein by reference in their entirety.

FIELD OF THE INVENTION

This invention relates generally to compositions, methods, and kits for joining together non-conjoined lumens in a patient's body including vascular lumens. More particularly, in various aspects, this invention provides compositions, methods, and kits for joining such non-conjoined lumens, including small lumens typically requiring microsurgical techniques.

BACKGROUND OF THE INVENTION

Non-conjoined lumens arise in a variety of settings including surgical settings where the non-conjoined lumens are intentionally created or those arising from lacerations or puncture wounds. Intentionally created non-conjoined lumens include those arising during surgical repair of e.g., treatment of a blockage in a lumen by bypass procedures, attaching a synthetic graft or during free tissue transfer in cosmetic surgical settings. Anastomosis is conducted to surgically reconnect the open ends of the lumen. Examples of anastomosis procedures include anastomotic procedures on the vasculature, the vas deferens, the fallopian tubes, the urinary tract, tear ducts, bowel, mammary glands, alimentary ducts, pancreatic ducts, bile ducts, etc. In each case, the anastomosis procedure creates a channel for the flow of a body fluid there through.

The anastomosis may, for example, be end-to-end, end-to-side, and side-to-side. As is apparent from their names, anastomosis may involve various configurations. For instance, one tubular tissue may be joined side-to-end with two tubular tissues, creating a three-channeled tubular tissue construct.

In the surgical context, end-to-end anastomosis, as is apparent from its name, is a surgical procedure for connecting an end or distal portion of one tubular tissue structure to an end or distal portion of another tubular tissue structure, such that a continuous lumen is created. (As used herein, "end" or "distal portion", refers to the open end of the tubular tissue).

In an end-to-side anastomosis, a tubular tissue structure having a hole or open part is connected through the open part to an open or distal end of a tubular tissue to form a continuous lumen with a branched configuration. Similarly, in a side-to-side anastomosis, two non-conjoined lumens are merged together into a continuous lumen though a hole or opening on each of the lumens to be joined.

A successful anastomosis typically involves the smooth connection of lumens, such that the internal structure is not blocked and internal body fluid flow—such as blood, semen or food or gastrointestinal fluids—is restored or improved. Ideally, the matching up/ligation surgical procedure is rapid and precise, so that patient exposure while in a vulnerable state—such as having blood flow stopped—is minimized.

There are a variety of "tubular tissues", and the lumen of the first tubular tissue may not be of the same diameter as the lumen of the second tubular tissue. Thus, because the delicate surgery may involve matching and ligating two (or more) non-identical tubular tissues, various ligation techniques have been used with varying rates of success. These include sutures, tissue adhesives, adhesive strips, and staples, clips and other devices. To some extent all of these materials involve the skill of the practitioner in anastomosis which is accurate, durable and free from conditions which could cause latent deleterious reactions in vivo.

The labor-intensive needle and thread remains the most-used technology as of the present day. Because of the complexity and judgment required in suturing, automated techniques are not well accepted. Calcified and diseased vessels provide mechanical challenges. Sutures may, in some instances, cause a reaction resulting in long term stenosis or fibrosis.

Other approaches to anastomosis include the use of sealants and bioglues for ligation. These may be used individually or in conjunction with suturing or other mechanical ligation techniques or devices. For example, one commercially available sealant CoSeal® (Angiotech Pharmaceuticals, Inc., Vancouver, B.C., CA) may complement suturing in cardiovascular surgeries.

Mechanical anastomosis devices, such as clips, are also available. One commercially available device, the U-Clip™ (Medtronic, Minneapolis, Minn. 55432 USA), essentially provides a sharp, nitinol hook for knotting to compete anastomosis. The nitinol allows reversible deformation. The C-Port® (Cardica, Inc. Redwood City, Calif. 94063 USA) and related products are commercially available and use miniature stainless steel staples to securely attach the bypass graft to the coronary artery.

But, before ligating end-to-end (for example), the practitioner must match up the lumens by the circumference of the vessel (using blood vessels as an illustration). Frequently, this is troublesome to the practitioner because the end of an tubular tissue—such as a clamped blood vessel devoid of blood—is not a perfectly round circle; rather it is in its unpressurized, deflated-looking state where a cross-sectional view of the circumference may be a circle, an oval or irregular, and, of course having no structural support from within, is unstably in any shape (unless the surrounding tissue possesses structural strength). The size of the vessels to be so connected may be different. Although blood vessels (for example) or other tubular tissues are somewhat elastic (deformable and returning to the original shape) or plastic (deforming, and not fully returning to the original shape), connecting the circumferences of the lumens such that upon ligation there is no or minimal leakage (in the vascular context, for example), requires a skilled practitioner.

In a microvascular context, anastomosis is performed between ends of blood vessels in the course of, for example, reattaching severed body parts or transplanting organs. Microvascular anastomosis is often performed by hand under a microscope, and is tedious and painstaking work. The blood vessels connected together often have different diameters, both of which are very small, on the order of about 1 to about 5 millimeters ("mm"). Although blood vessels are usually at least somewhat elastic, the practitioner must match up end to end (for example) two different shaped-different-sized circumferences and then stitch them together (for example). As a result, it can take many hours to complete just the microvascular anastomosis required to reconnect a severed body part or transplant an organ.

One attempt to provide a mechanism for performing such a microvascular anastomosis is the Microvascular Anastomotic Coupler System, available from Bio-Vascular, Inc. (San Diego, Calif., USA). In this mechanism, an end of each vessel to be connected is essentially turned outward ("everted") over a ring with a forceps or similar instrument. Each ring includes a number of pins over which the vessel is everted. The rings are then pressed together, such that the pins on each ring enter recesses in the other ring, connecting the rings and holding the ends of the vessels together. This system, however, is limited to use with two blood vessels having substantially the same diameter. Further, manual eversion of a blood vessel having a diameter on the order of one millimeter is difficult and painstaking, particularly when the eversion is to be substantially even around the circumference of the ring. Further, the rings provide a noncompliant anastomosis between the two vessels. Thus, although stabilizing the circumference facilitates the ability of the practitioner to match up vessels for end-to-end microvascular anastomosis, the device requires, essentially, practitioners skilled in microsurgical techniques.

For patients and practitioners, perhaps the most demanding anastomosis is incident to heart revascularization. The arteries that bring blood to the heart muscle (coronary arteries) can become clogged by plaque (a buildup of fat, cholesterol and other substances). This can slow or stop blood flow through the heart's blood vessels, leading to chest pain or a heart attack. Increasing blood flow to the heart muscle can relieve chest pain and reduce the risk of heart attack. A patient may undergo one, two, three or more bypass grafts, depending on how many coronary arteries are blocked.

Coronary artery bypass graft surgery ("CABG", sometimes pronounced "cabbage" by practitioners) reroutes, or "bypasses," blood around clogged arteries to improve blood flow and oxygen to the heart. In performing the CABG anastomosis, a segment of a healthy blood vessel from another part of the body is used to make a detour around the blocked part of the coronary artery. This healthy blood vessel may be, for example, an artery present in the thoracic cavity, or may be a piece of a long vein from the patient's leg. In some circumstances, grafts from non-autologous sources may be used, such as synthetic tubular tissues or animal tubular tissues. Regardless of the source of the healthy blood vessel, one end is connected to the large artery leaving the patient's heart (the aorta), and the other end is attached or "grafted" to the coronary artery below the blocked area. In this way of "rewiring" the vasculature, substantially unobstructed blood flow to the heart muscle is resumed.

Conventionally, a pump oxygenator (heart-lung machine) is used for coronary bypass graft operations. Medicines are used to stop the patient's heart, which allows the practitioner to operate without the heart beating. The heart-lung machine keeps oxygen-rich blood moving throughout the patient's body. For this conventional heart bypass graft surgery, a team of practitioners is needed (a surgeon, cardiac anesthesiologist and surgical nurse, and a perfusionist (blood flow specialist)). Multiple practitioners, additional complexity, and, as a practical matter, additional health care cost is involved over surgical procedures involving fewer practitioners and procedures.

Moreover, blood quality may be degraded as the heart-lung machine repetitively pumps the patient's blood through the systemic circulation. The blood may embolize or clot in the distal circulation, or form clots which migrate to the distal vasculature, and cause a stroke.

"Off-Pump" coronary artery bypass grafting, also called beating heart bypass grafting, takes place while the heart continues to beat, but a mechanical device may be used in an attempt to steady the surrounding vasculature, so that the practitioner can perform the graft. Off-pump coronary artery bypass surgery may reduce this risk. Frequently, because the graft must be performed on arteries in locations directly affected by the beating heart, stabilizing mechanisms are not thoroughly effective, and the practitioner must suture the graft while the graft is moving in conjunction with the heart beat, at least to some extent. Thus, the graft quality may be compromised.

Although, in a bypass surgery time is of the essence, the practitioner cannot rush through without thoroughly and precisely anastomising the graft(s). In conventional coronary artery bypass surgery, three critical determinates that affect the outcome of a bypass surgery are:

(1) time the patient spends on cardiopulmonary bypass,
(2) time the patient spends with a clamped aorta, and
(3) the quality of the anastomosis.

After an hour, the risk of patient morbidity is thought to increase perhaps due to the heart-lung machine degrading the quality of the blood as it is circulated through the systemic circulation. Bypass surgeries, however, often last three hours or longer. Moreover, where the aorta is clamped and blood therefore cannot pass through, the blocked blood is thought to cause additional issues.

Anastomosis is time-consuming. The average time for suturing one anastomosis is approximately fifteen to sixty minutes. An average CABG procedure is thought to involve approximately five anastomoses. Therefore, the average time for graft suturing exceeds the sixty-minute threshold for patient morbidity. Patients treated with conventional coronary surgery and placed on cardiopulmonary bypass would benefit from reducing the amount of time spent performing each anastomosis.

In "off pump" procedures where the heart remains beating, the difficulty of suturing an anastomosis graft on a moving surface of the heart may degrade the quality of such grafts completed on patients. An anastomosis differs from straight line suturing in that each suture has a different orientation that is based on its position around the cross-sectional circumference of the blood vessel graft. It can be appreciated that some of the sutures are easily made from on top of the conduit or blood vessel graft, while others are more difficult to complete as they are beneath the conduit. It can be further appreciated that performing such complex suturing procedures on a moving platform, such as the beating heart, further increases the difficulty associated with such suturing procedures. Improperly connecting blood vessel grafts to the patient may present substantial post-operative complications and/or increase operating room time spent correcting the improperly connected graft.

Accordingly, for surgical anastomosis, both practitioners and patients would benefit from faster procedures allowing patients to minimize procedure time, and simpler methods allowing reduced complexity and ease of use and higher quality anastomosis with fewer complications.

SUMMARY OF THE INVENTION

This invention is directed to the discovery that the stabilization of the geometry of the terminal portions of tubular tissues facilitates joining such non-conjoined tissues. In one aspect, such stabilization is achieved by use of biocompatible solid materials which can be placed into the terminal portions of at least one of the lumens of the tubular tissues to be joined.

Thus, in one aspect, this invention relates to a method for joining at least two non-conjoined lumens in a patient which method comprises:

a) providing a biocompatible solid mass in at least the distal portion of at least one of the lumens;

b) aligning the lumens;

c) joining the aligned lumens to form a conduit; and d) removing the solid mass thereby establishing flow through the conduit.

In one embodiment, the solid mass is placed in the distal portion (opening) of each lumen to be joined. In another embodiment, the solid mass is placed in the distal portion of a first lumen in a manner in which the solid mass protrudes from the distal portion such that this protrusion can be used as a male mating functionality with the distal portion of the second lumen which acts as a female mating functionality.

The biocompatible solid mass employed in the methods described herein is not critical provided that it imparts sufficient structural integrity to the distal portion of the lumen. Examples of suitable solid masses include sol-gel solutions, waxes, thixotropic agents, etc.

The removal of the solid mass can be accomplished using any of a number of physical properties of the mass such as melting, phase change, change in viscosity, dissolution in the body fluid and/or combinations of these properties.

Accordingly, in another of its method aspects, there is provided a method for joining at least two non-conjoined lumens having distal (open) ends, comprising the steps of:

providing a phase-reversible sol-gel inside at least a portion of the distal end of the first lumen in a manner which imparts structural integrity to said portion of the first lumen;

providing a phase-reversible sol-gel inside at least a portion of the distal end of a second lumen in a manner which imparts structural integrity to said portion of the second lumen;

aligning the distal portions of the first and second lumens;

joining said lumens so as to provide for a conduit;

inducing a phase change in the phase-reversible sol-gel in said conduit wherein said sol-gel phase changes to a liquid phase; and allowing flow through said conduit.

In still another of its method aspects, there is provided a method for joining at least two non-conjoined lumens having distal (open) ends, comprising the steps of:

providing a phase-reversible sol-gel inside at least a portion of the distal end of a first lumen in a manner which imparts structural integrity to said portion of the first lumen wherein said sol-gel protrudes from the distal end;

mating the distal end of a second lumen with said protrusion from the first lumen thereby aligning the first and second lumens;

joining said lumens so as to provide for a conduit;

inducing a phase change in the phase-reversible sol-gel in said conduit wherein said sol-gel phase changes to a liquid phase;

allowing flow through said conduit.

In another of its method aspects, there is provided a method for joining at least two non-conjoined lumens having distal (open) ends, comprising the steps of:

providing a solid biocompatible wax inside at least a portion of the distal end of the first lumen in a manner which imparts structural integrity to said portion of the first lumen;

providing a solid biocompatible wax inside at least a portion of the distal end of a second lumen in a manner which imparts structural integrity to said portion of the second lumen;

aligning the distal portions of the first and second lumens;

joining said lumens so as to provide for a conduit; and converting the wax from a solid to a dissolved and/or liquid form such that flow is established through said conduit.

In still another of its method aspects, there is provided a method for joining at least two non-conjoined lumens having distal (open) ends, comprising the steps of:

providing a solid biocompatible wax inside at least a portion of the distal end of a first lumen in a manner which imparts structural integrity to said portion of the first lumen which wax protrudes from said distal end;

mating the distal end of a second lumen with said protrusion from the first lumen thereby aligning the first and second lumens;

joining said lumens so as to provide for a conduit; and converting the wax from a solid to a dissolved and/or liquid form such that flow is established through said conduit.

In another of its method aspects, there is provided a method for joining at least two non-conjoined lumens having distal (open) ends, comprising the steps of:

providing a solid biocompatible thixotropic agent inside at least a portion of the distal end of the first lumen in a manner which imparts structural integrity to said portion of the first lumen;

providing a solid biocompatible thixotropic agent inside at least a portion of the distal end of a second lumen in a manner which imparts structural integrity to said portion of the second lumen;

aligning the distal portions of the first and second lumens;

joining said lumens so as to provide for a conduit; and converting said thixotropic agent from a solid to a dissolved and/or liquid form such that flow is established through said conduit.

In still another of its method aspects, there is provided a method for joining at least two non-conjoined lumens having distal (open) ends, comprising the steps of:

providing a solid biocompatible thixotropic agent inside at least a portion of the distal end of a first lumen in a manner which imparts structural integrity to said portion of the first lumen which agent protrudes from said distal end;

mating the distal end of a second lumen with said protrusion from the first lumen thereby aligning the first and second lumens;

joining said lumens so as to provide for a conduit; and converting said thixotropic agent from a solid to a dissolved and/or liquid form such that flow is established through said conduit.

In still another of its method aspects, there is provided a method of connecting ducts within a living mammal, comprising the steps of:

providing a phase-reversible gel inside a first hollow duct in a manner which holds the first duct open;

providing a phase-reversible gel inside a second hollow duct in a manner which holds the second duct open;

applying adhesive between an end of the first duct and an end of the second duct and allowing the adhesive to form bonds between the first and second ducts;

inducing a phase change in the phase-reversible gel inside the first duct and inside the second duct; and allowing flow through the first duct to the second duct.

In some embodiments, the adhesive is further placed on the out surface of both ducts to join them together.

This invention is also directed to novel compositions useful in the methods described above. For example, in one embodiment, this invention is directed a thermoreversible sol-gel, comprising:

a) a biocompatible polymer and b) water;

wherein the thermoreversible so-gel has a sol-gel transition temperature of from about 35° C. to 42° C. and a modulus of from at least about 100 to about 500,000 Pascals.

In one embodiment, the polymer is a block co-polymer of polyoxyethylene and polyoxypropylene or mixtures of such block copolymers. In another embodiment, the composition is sterile.

In another aspect, the thermoreversible sol-gel further comprises a biocompatible protein which increases the phase transition temperature of the composition while the structural integrity of the sol-gel modulus in the gel state.

In still another embodiment, the solid mass may contain a biocompatible dye so as to facilitate the alignment of the first and second lumen.

This invention is also directed to novel kits useful in the methods described above. In one embodiment, the kit comprises a delivering device; and a composition selected from a sol-gel, a wax, and a thixotropic material. In another embodiment, the kit further comprises at least one clamp for closing at least one of the non-conjoined lumen. In still another embodiment, the kit further comprises a biocompatible adhesive for sealing the lumens.

The present invention also includes use of any of the materials or methods as disclosed herein for manufacture of a medicament for joining lumens, particularly in a live patient, as further described herein. Thus, in one embodiment, the present invention provides a biocompatible solid mass for use in joining at least two non-conjoined lumens in a patient in a method which comprises:

a) placing the a biocompatible solid mass in at least the distal portion of at least one of the lumens;

b) aligning the lumens;

c) closing the aligned lumens to form a conduit; and d) removing the solid mass thereby establishing flow through the conduit.

The methods, compositions and kits of this invention may be used in both human and non-human mammals.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 3 is a schematic cross-sectional view of the tubular tissue of FIG. 1 with one end filled with thermoreversible sol-gel (solid or gel phase) and the other end being filled with the sol-gel (liquid phase) via a syringe.

FIG. 4 is a schematic cross-sectional view of the tubular tissue of FIG. 1 with the ends sealed, the gel (solid phase) in place and the clamps still present.

DETAILED DESCRIPTION OF THE INVENTION

Figure 1:
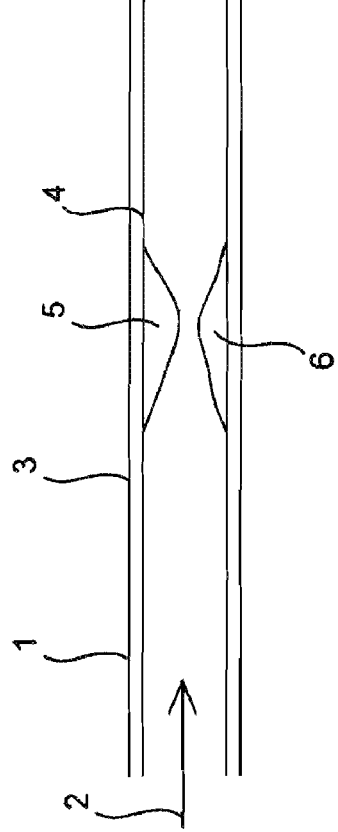
FIG. 1 is a schematic cross-sectional view of a tubular tissue with a partial blockage.

Before the present compositions, medical systems, kits, and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a thermoreversible gel" includes a plurality of such gels and reference to "the adhesive" includes reference to one or more adhesives and equivalents thereof known to those skilled in the art, and so forth.

I. Definitions

Unless defined otherwise, all technical and scientific terms used herein have the same meaning as commonly understood by one of ordinary skill in the art to which this invention belongs. As used herein the following terms have the following meanings. If not defined, a term has its art recognized meaning.

The term "lumen" refers to the hollow tube and the surrounding tissue defining the hollow tube, such as a blood vessel, a vas deferens, a fallopian tube, urinary tract, a tear duct, bowel, a mammary gland, an alimentary duct, a pancreatic duct, a bile duct, and the like. The term "lumen" is used interchangeably with the term "duct."

The term "biocompatible" as used with terms such as "biocompatible polymer", "biocompatible compound" and the like, refer to materials which, in the amounts employed, are non-toxic and substantially non-immunogenic when used internally in a subject such as a human patient.

The term "biocompatible solid mass" refers to a biocompatible mass having sufficient structural rigidity to maintain the shape of the filled lumen during joining of the distal opening of a first and second lumen and which solid mass can be subsequently removed from the joined lumens so as to permit flow there through. Examples of biocompatible solid masses include sol-gel compositions, waxes, thixotropic agents, and the like. In a preferred embodiment, the solid mass has a modulus of from about 100 to 500,000 Pascals or a yield stress of about 100 to 500,000 Pascals for the thixotropic solid mass. More preferably, the solid mass has a modulus or a yield stress of from about 100 to 10,000 Pascals and, still more preferably, from about 150 to 1500 Pascals.

The term "distal end" and "opening" of a lumen are used interchangeably herein and refer to the opening of the lumen, for example, the two ends created when a lumen is surgically divided into two parts. "Distal end" or "opening" also refers to a hole cut on part of the wall of a lumen although the lumen is not completely divided, as in the case of an end-to-side or side-to-side anasotomosis.

The term "distal portion of the lumen" refers to the portion of the lumen adjacent to the opening in the lumen. Thus, for example, when a lumen is surgically cut, the resulting two openings define the distal portion of what are now first and second lumens. Distal portion of the lumen also refers to the portion adjacent to the hole of a lumen to be used in an end-to-side or side-to-side anasotomosis procedure. In surgical procedures where a clamp is employed on each of the non-conjoined lumens, the distal portion is the portion from the clamp to the end of the open lumen.

The term "joining" refers to any method wherein the first and second lumens are structurally joined together including by way of example, suturing, use of biocompatible glues, etc. In a preferred embodiment, joining of the lumens is conducted under conditions where there is little or no leakage of body fluid from the juncture of the joined lumens.

The term "removing the solid mass" refers to any of a number of physiological or chemical means to remove the solid mass from the conduit formed by the joined lumens. For example, the solid mass may be removed by melting as in the case of waxes having a melting point at or slightly above body temperature. Alternatively, the wax may be soluble in the body fluid when flow is restored in the joined lumens. Still further, a combination of melting and dissolution can be used. Thixotropic agents will significantly reduce their viscosity in the presence of shear forces and become fluid in nature. As such, in this case, removing the solid mass of a thixotropic agent can involve either internally applied shear such as that arising from restoring flow or externally applied shear. Sol-gel compositions undergo a phase transfer from a solid to a liquid under defined phase transfer triggers such as temperature, pH or other ion concentration, light, etc. In such cases, conventional triggers are employed to effect phase transfer from a solid to a liquid. Such liquids will be engrained in the body fluid and become part of the systemic flow of that fluid until removed by the body.

The term "sol-gel" refers to a composition, typically polymeric, which, upon a defined trigger, undergoes a phase transition from a flowable composition with a viscosity of less than 2000 Pascal-seconds ("liquid") to a gel or relatively solid form with a viscosity of greater than 10,000 Pascal-seconds ("gel" or "solid") which transition is preferably but not necessarily reversible. When reversible, the composition is referred to as a "phase-reversible sol-gel". Preferably reversing phase from a solid to a liquid occurs in less than 5 minutes, more preferably in less than 2 minutes and even more preferably in less than 1 minute.

The term "trigger" or "stimulus" refers to the environmental condition that triggers the phase transition from sol to gel or vise versa. One embodiment of this invention comprises an aqueous-based solution or compound having low viscosity at physiological conditions, but exhibiting rapid gelation at conditions slightly outside of (e.g., ±2% to ±10%) physiological conditions. In the case of temperature as a stimulus, the transition from a liquid state to gelled state may occur at temperatures that are slightly outside (e.g., ±2% to ±10%) physiological temperatures. Such temperatures are referred to as "near" the normal physiological body temperature. The flowable liquid solution gels in response to one or multiple in-situ environmental stimuli, and may be reversible. The composition should have biocompatibility with the host tissue. The invention is preferably carried out with a composition which is comprised only of biocompatible materials and more preferably materials approved by regulatory agencies.

Although the working example herein is a thermoreversible sol-gel composition, using temperature to initiate phase-transition, other sol-gel compositions systems may be similarly used, and may be selected with regard to the particular anastomosis use. For example, the phase change may be due to other stimuli such as pH, ion concentration (e.g., a change in calcium ion concentration) or light. The sol-gel compositions may be deployed in either a substantially solid or substantially liquid state. Although the terms "substantially solid" and "substantially liquid" are relative with respect to each other, in the context of anastomoses where the utility lies, in part, in structural support for the geometry of the terminus of a tubular tissue, "substantially solid" is used herein to mean that the sol-gel is sufficient to provide such structural support; "substantially liquid" is used herein to mean that the sol-gel is insufficiently solid to provide such structural support.

For example, where tubular tissue is very narrow, a practitioner may wish to deploy the sol-gel via injection, as presented in further detail herein.

The terms "adhesive", "surgical adhesive", "glue", "biocompatible glue" and the like are used interchangeably herein. These terms are used to describe compounds which are or can be used in binding one tissue to another tissue. The glue may operate by the formation of covalent bonds and allow the tissues to contact each other and naturally heal or grow together. The adhesive may be comprised of a cyanoacrylate-based adhesive, a fibrin-based adhesive, a polyurethane-based adhesive, a polyisocyanate-based adhesive. The polyurethane-based adhesive may include a foaming agent added to produce an open cell geometry upon curing in situ to promote tissue ingrowth. Adhesive materials may be found within publications known to those skilled in the art and reference made to U.S. Pat. No. 7,044,982 issued May 16, 2006 and U.S. Pat. No. 6,939,364 issued Sep. 6, 2005. Both of which are incorporated herein by reference along with the publications cited therein to disclose and describe surgical adhesives to the extent that these disclosures do not contradict the present disclosure.

II. Solid Mass Compositions

Sol-Gel Composition Moieties

A variety of sol-gel compositions are known in the art, and have various phase transition properties. One will appreciate that various properties may be altered by changing the constituents or constituent ratios in any sol-gel. Persistence properties and mechanical properties may be altered, including the degree to which the present sol-gels liquefy or solidify, the nature or range of phase-transition initiation or stimulus, the persistence and the mechanical properties. The sol-gel may, for example, include particulate materials which may increase the persistence, as further described herein.

"Thermoreversible sol-gel" refers to a composition that undergoes a phase transition from a liquid flowable material to a solid or gel like material when the temperature is raised to or above a transition temperature, and undergoes a phase transition from a solid or gel like material to a liquid flowable material when the temperature is lowered to or below the transition temperature. Such phase-transition is reversible.

The following references disclose processes or compounds useful in this art: U.S. Pat. Nos. 5,525,334; 5,702,361; 5,695,480; 5,858,746; 5,589,568. Dumortier et al., "A Review of Polexamer 407" Pharmaceutical Research, Vol. 23, No. 12 (December 2006). T. G. Park and A. S. Hoffman, "Synthesis, Characterization, and Application of pH/Temperature-sensitive Hydrogels", Proceed. Intern. Symp. Control. Rel. Bioact. Mater., 17 (1990), pp. 112 113. G. Chen and A. S. Hoffman, "Graft Copolymers That Exhibit Temperature-induced Phase Transitions Over a Wide Range of pH", Vol. 3, Nature, 1995, pp. 49 52. S. Beltran, J. P. Baker, H. H. Hooper, H. W. Blanch and J. M. Prausnitz, "Swelling Equilibria for Weakly Ionizable, Temperature-Sensitive Hydrogels", Proc. Amer. Chem. Soc., 1991. J. Zhang and N. A. Peppas, "Synthesis and Characterization of pH- and Temperature-Sensitive Poly(Methacrylic acid)/Poly(N isopropylacrylamide) Interpenetrating Polymeric Networks, Macromolecules, 2000 (currently available on-line on the world wide web). T. G. Park, "Temperature Modulated Protein Release From pH/Temperature Sensitive Hydrogels; Biomaterials 20 (1999), pp. 517-521.

Examples of sol-gel compositions include biocompatible ethylene oxide propylene oxide co-polymers which are typically prepared as block copolymers and are otherwise known by their tradenames such as Pluronics®, Pluronic F127®; Polyethylene-polypropylene glycol; Polyoxyethylene-Polyoxypropylene Block Copolymer; Poly(Ethylene oxide-co-Polypropylene oxide), Block; BlockCopolymer of Ethylene Oxide and Propylene Oxide and other names. Such polymers are commercially available from a number of sources and can be made by conventional synthetic methods. Other examples of biocompatible sol-gel compositions include, without limitation, block copolymers of polyethylene glycol with a polymer selected from polyester, poly(lactide-co-glycolide), poly(a-hydroxy acids) and poly(ethylene carbonates), described in U.S. Pat. Nos. 7,018,645, 6,004,573 and 5,702,717; poly N-substituted (meth)acrylamides, described in U.S. Pat. No. 5,525,334; modified polysaccharides, described in U.S. Pat. No. 6,018,033; and copolymers described in U.S. Pat. No. 7,160,931.

The molecular weight of the polymer in the sol-gel composition may be in the range of about 8,000 to 16,000, more preferably 10,000 to 16,000, or more preferably 10,000 to 14,000 and most preferably about 12,600. The term "about" as used in this context reflects that commercial preparations of the monomers or polymers as described herein may contain mixtures of varying molecular weights incident to the commercial manufacturing process.

As more fully described herein, the thermo-inducible phase transition may be altered by the addition of a polypeptide or a protein; as such, if proteins are added for biological activity (such as a protein having therapeutic effect), the practitioner will note that the phase-transition property of the underlying polymer may be altered. Alternatively, the protein may be added to effect a change in transition temperature of a composition otherwise having the requisite modulus. Such proteins are non-therapeutic and preferably non-immunogenic. In one embodiment, the protein is albumin such as BSA or HSA. Recombinant versions of such proteins (or any proteins as described herein) may be preferred for commercial manufacturing reasons, for assurance of no animal-originating pathogenic agents.

Other compositions useful as the solid mass in this invention include a variety of hydrogels, which are water-insoluble three-dimensional networks that formed by the cross-linking of water-soluble monomers. Either synthetic or natural polymers may be used. Useful synthetic materials are poly(lactic acid) (PLA), poly(glycolic acid) (PGA), and their copolymers, poly(lactic co glycolic acid) (PLGA). Such compositions are well known in the art.

In situ cross linking (and/or polymerization) can be used to increase rigidity. Therefore, for anastomosis of an individual, the crosslinking is able to take place under physiologic conditions. Particularly for human uses, physiological conditions involve a temperature of about 37° C., and a pH of about 7.4. Suitable cross linking conditions will be chosen based on the chemical structure of the monomers to be polymerized, the desired mechanical and persistence properties of the hydrogel after polymerization, and other considerations as are well known in the art.

In one embodiment, the sol-gel composition is delivered into at least a portion of the distal end of the lumen in a solid form. In some circumstances, it is preferable that the delivered composition protrude from the lumen thereby providing a mating mechanism for the distal end of the other lumen so that aligning the distal ends of the two lumen is relatively easy.

Waxes

Other solid mass materials useful in this invention include biocompatible waxes.

The term "wax" as used herein means a relatively low-melting temperature, high-molecular-weight, organic mixture or compound, similar to fats and oils but lacking glycerides. See, Dorland's Medical Dictionary (2004, W. G. Saunders, herein incorporated by reference for various definitions under the "wax" listing).

As noted by Dorland's, waxes may originate from natural sources (e.g., insects or plants) or may be synthetics, and most are fatty acid esters and alcohols with some hydrocarbons. Other moieties may include lauric acid, myristic acid, palmitic acid, stearic acid, arachidic acid, lignoceric acid, palmitoleic acid, oleic acid, linoleic acid, linolenic acid, arachidonic acid and other biocompatible fatty acids that are endogenous to the treated patient as well as mixtures thereof.

The materials are not all-inclusive, and the principal useful feature herein is the ability of the wax to be "melted" or substantially liquefied with heat or dissolved in the body fluid once flow is reinstated, particularly in situ, at temperatures which are not injurious to live tissue (if used pursuant to a surgical procedure on a live patient). The melting point of the waxes can be adjusted by conventional melting point depression by mixing two or more waxes together. For example, lauric acid has a melting point of 44.2° C. and slight depression of this melting point by mixing with another suitable fatty acid can bring the melting point down to 40 to 42° C. Low temperature polyester waxes, such as "Steedman's wax" which have a melting temperature of about 37° C. (human body temperature) may be used in some circumstances. See, Steedman, H. F., Nature 179:1345 (29 Jun. 1957).

In one embodiment, the wax can be preformed into a "stick" configuration of predetermined diameters. The clinician can then insert a portion of the wax into a first lumen with the remaining portion providing a mating mechanism for the distal end of the other lumen so that aligning the distal ends of the two lumen is relatively easy.

For microsurgical techniques involving human or other mammalian blood vessels, the diameter of between about 0.5 and 1.5 mm is probably suitable. For other purposes, such as intestinal anastomosis or large venous surgeries, the diameter may be several centimeters ("cm"). (Although the term "diameter" is used, if the biocompatible stick is not cylindrical, the area of the surface of the terminus is the relevant measurement for determining what will fit into distal termini of tubular tissue.)

Thixotropic Agents

Still other solid mass materials useful in this invention include thixotropic or other non-Newtonian fluidic agents. These materials use deformation, or shear stress, for phase change along the solid to fluid (or vice versa) continuum.

In general, for fluids demonstrating non-Newtonian dynamics, viscosity changes with applied stress or applied shear rate. Thixotropic, or other non-Newtonian fluids, become more or less viscous with applied movement. For example, some thixotropic agents become less viscous subjected to stresses above a critical level. These shear-thinning fluids may be inserted into immobilized tubular tissues to stabilize the distal ends as described herein. Upon joining, movement may be applied to the now-sealed tissues to liquefy the thixotropic agent. These stresses may be applied externally or may arise naturally from the peristaltic pressure in the circulatory system. Thixotropic agents include various bioabsorbable or dissolvable clays, materials with corn starch or other carbohydrate-based materials, and other colloidal and other materials as are available to those of skill in the art. It is contemplated that the thixotropic agents suitable for use in the present invention will have a yield stress of from about 100 to about 500,000 Pascals, preferably from about 100 to about 10,000 Pascals, and even more preferably from about 150 to about 1,500 Pascals.

Thus, as thixotropic agents are used herein for their relatively solid form in supporting distal termini in tubular tissues, it may be initially deployed in a less viscous state, and allowed to "rest" or not be subject to shear-thinning movement. Upon satisfactory adjoining of the tissues, shear-thinning stress may be locally applied.

Additional Moieties

The solid mass compositions used in the methods of this invention may include one or more additional moieties. For example, a biologically functional agent, a dye and/or a contrasting agent may be added to the solid mass to provide additional functionalities for the solid support.

Biologically active moieties or agents may include, without limitation:

antithrombotic agents, such as coagulants (for example heparin), platelet inhibitors, and thrombolytic agents;
anti-anginals, such as beta-blockers, calcium channel blockers, and nitrates;
antiinfectives, such as antibiotics, antiviral and antifungal agents;
analgesics and analgesic combinations;
antiinflammatory agents;
antiarrhythmics;
antihypertensives;
heart failure agents;
wound healing agents;
antiasthmatic agents;
antidiuretic agents;
antineoplastics;
antipyretics;
antispasmodics;
anticholinergics;
immunosuppressives;
sympathomimetics;
central nervous system stimulants;
parasympatholytics;
hormones such as growth hormones, estradiol and other steroids, including corticosteroids;
muscle relaxants;
lipid lowering agents;
anti-ulcer H2 receptor antagonists,
anti-ulcer drugs;
anorexics;
antiarthritics;
sedatives; and
tranquilizers.

The biologically active moiety may optionally be therapeutically effective as administered, and the subject solid mass may optionally contain a therapeutically effective amount of the biologically active moiety.

A therapeutically active moiety will be a biologically active moiety. A therapeutic effect is one which seeks to treat the source or symptom of a disease or physical disorder. The term "treat" or "treatment" as used herein refers to: (i) preventing a disease or disorder from occurring in a subject which may be predisposed to the disease or condition but has not yet been diagnosed as having it; (ii) inhibiting the disease or disorder, i.e., arresting its development; and/or (iii) ameliorating or relieving the disease or disorder, i.e., causing regression of the disease. A therapeutically effective amount is sufficient to establish causation of a therapeutic effect, as determined by relevant clinical standards. The therapeutically effective amount will vary depending upon the specific agent incorporated, the subject and disease condition being treated, the weight and age of the subject, the severity of the disease condition, the dosing regimen to be followed, timing of administration, the manner of administration and the like, all of which can be determined readily by one of ordinary skill in the art.

Biologically active moieties may also be incorporated into the ligation (joining) composition applied to the tubular tube tissue so adjoined incident to the anastomosis. As described herein, ligation can be accomplished any number of ways, and, if the present anastomosis materials are used, sutures or an adhesive may be most practicable.

Contrast agents, such as a biocompatible radio opaque material capable of being monitored by, for example, radiography, may also be added to the solid mass to track and monitor the solid mass and/or the procedure. The contrast agent may be water soluble or water insoluble and preferably does not contain radioactivity above the native or endogenous amounts naturally occurring in the elements employed.

Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a preferred particle size of about 10 microns or less. Other water insoluble contrast agents include gold, tungsten, and platinum powders.

The solid mass compositions may also include a suitable biocompatible dye for visualization, especially when a lumen has a thick wall. Such dyes are well know in the art.

III. Anastomosis Methods

It is contemplated that the present invention can be applied to any anastomotic procedure that connects one hollow tissue structure (lumen) to another hollow tissue structure (lumen), such that the spaces within each hollow tissue structure are connected thereby forming a conduit (an intraluminal conduit). It can be used in a microvascular context, which is performed between ends of blood vessels in the course of, for example, reattaching severed body parts and/or transplanting organs. It can be used to connect non-conjoined lumens arising from surgical procedures wherein the originally intact lumen has been severed for the purposes of, e.g., removing a blockage or partial blockage. Suitable lumens include, by way of example, the vasculature, the vas deferens, the fallopian tubes, the urinary tract, tear ducts, bowel, mammary glands, alimentary ducts, pancreatic ducts, bile ducts, etc. (Specific anatomical lumens may be referenced by their conventional anatomical nomenclature such as tubes, ducts or vessels, as used in context herein.)

In one embodiment used for illustrative purposes only, the anastomosis is performed during coronary artery bypass graft (CABG) procedures or peripheral bypass procedures to connect two blood vessels or one blood vessel with one synthetic graft. The blood vessels connected together may have different diameters. Further one or both of the vessels may be very small, and may be on the order of about 1 to 5 millimeters ("mm"). The microvascular anastomosis procedure using the present invention may be performed under a microscope.

Referring now to the Figures, the invention is described schematically and in a simplistic fashion in order to convey the general concepts. With these concepts in mind those skilled in the art will contemplate detailed specific embodiments of the invention which are intended to be encompassed by the present claims. FIG. 1 shows a schematic cross-sectional view of a lumen which may be a vessel 1 which has flow 2 running there through. A portion of the vessel indicated by points 3 and 4 has a restricted flow due to the formation of blockages 5 and 6. The blockage may become so severe that the flow is completely blocked. Those skilled in the art will appreciate that a range of different treatments are available for restoring flow.

Prior to the operation to restore flow, the vessel needs to be occluded to stop the fluid (e.g., blood) flow. Such occlusion is important for anastomosis involving a blood vessel to prevent excessive loss of blood and complications caused by a continuous blood flow. However, clamping may not be necessary for anastomosis of other types of lumens where there is no continuous flow of fluid or the amount of fluid does not complicate the procedure.

Figure 2:
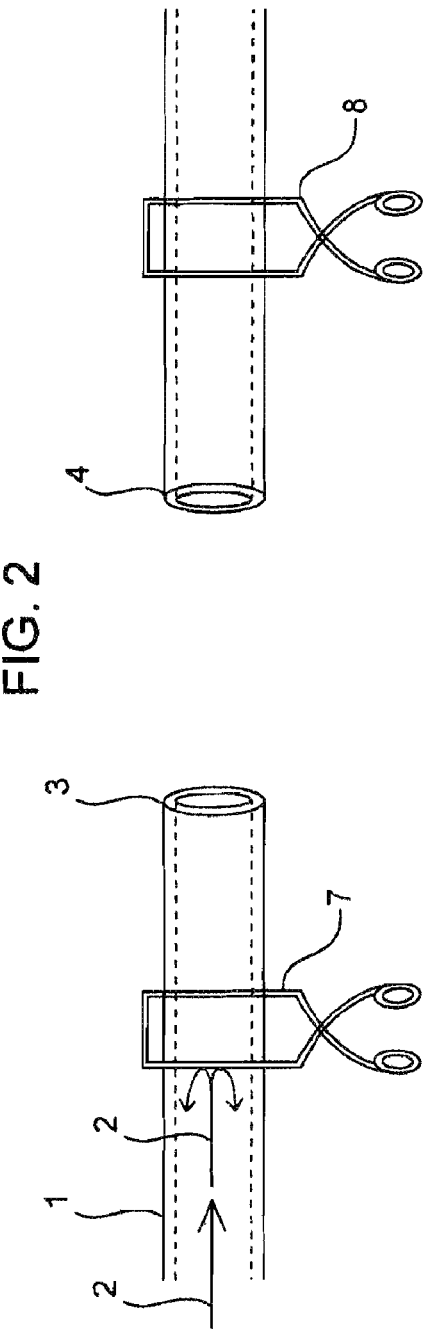
FIG. 2 is a schematic cross-sectional view of the tubular tissue of FIG. 1 wherein the area having the partial blockage has been removed creating two non-conjoined lumens having both ends of the tubular tissue clamped off.

Thus, as shown in FIG. 2, clamps 7 and 8 have been placed on the vessels to stop the blood flow in the section between the clamps prior to removal of the blocked section. Such clamps can be any surgical clamps suitable for clamping the vessels to be operated on from the outside, such as clamps, clips and tourniquets or snares. After clamping, a portion of the vessel 1 which has the restricted flow between the points 3 and 4 is then surgically removed. Those skilled in the art will understand that the distance between the points 3 and 4 is sufficiently small such that the ends can be brought into contact with each other to restore flow.

Referring now to FIG. 3, the inside of the vessel 1 between the clamp 7 and the end 3 has been filled with the phase-reversible sol-gel 10 which is shown in solid phase by the crossed markings. The area between the clamp 8 and the end 4 is being filled with sol-gel 11 in a liquid phase. The sol-gel is injected from a suitable source such as a hypodermic needle 9. When the sol-gel material is in the hypodermic needle it may be either in a flowable liquid phase or in a gel phase. In the former case, the composition will undergo a phase transition to a solid gel phase (10) upon the application of the suitable environmental stimuli such as heat. In the latter case, the composition is delivered in a solid gel phase (10) and maintained in that phase by continuing the application of the suitable environmental stimuli such as heat.

The sol-gel material is included in a sufficient amount so as to maintain at least a portion of the distal end of vessel 1 open. In the absence of some force, the side walls of the vessel 1 will contact each other and cause the vessel to close in the absence of flow through the vessel. The solid gel phase (10) imparts sufficient structural rigidity to the lumen to permit the anastomosis to proceed with the vessel in its fully filled form.

As shown in FIG. 4, the two lumens are joined by applying an adhesive or glue 12 on the two ends of the lumens as well as on the outer surface of the vessel at points 3 and 4 and sealed together. Although FIG. 4 shows the use of a glue, it is to be understood that as described herein, joining or ligation can be accomplished any number of ways, and, if the present anastomosis materials are used, sutures or an adhesive may be most practicable. Sutures are well known in the art as are surgical glues or adhesives. Such glues are biocompatible and are generally cyanoacrylate-based adhesives, fibrin-based adhesives, a polyurethane-based adhesives, a polyisocyanate-based adhesives. The suture or glue may contain biologically active moieties such as antimicrobial agents (e.g., U.S. Pat. No. 5,762,919).

Due to the presence of the gel (in solid phase) significant amounts of adhesive can be used without resulting in vessel closure. In the absence of a structural support, such as the phase-reversible sol-gel 10 in this example, being present within the vessel the application of pressure to the outside of the vessel such as by the application of glue can cause collapse of the vessel. However, since the phase-reversible sol-gel 10 is holding the vessel open, glue can be applied liberally not only to the ends 3 and 4 which are to be sealed together but the glue 12 can be applied along the surface of the vessel 1 near the point where the seal is to take place. Thus, as shown in FIG. 4, glue has been applied on the outside of the vessel 1 on either side of the point where the ends are sealed. The glue can extend outward in any desired amount. However, with smaller vessels extending the glue out a distance of about 1 mm to about 10 mm is generally sufficient. The glue can extend outward around the entire circumference of the connecting point. After the adhesive 12 has been allowed to cure and seal bonds between the two ends of the vessel, the clamps 7 and 8 can be removed. In one embodiment the glue also penetrates inward to the surface of the gel thereby providing adherence of the entire tissue cross-section of the first lumen to the second lumen. In another embodiment, the glue is applied not only to the outer surface but also to the cross-sectional surfaces of the lumens to be closed. In a still further embodiment, a solid mass, such as a sol-gel, has a superior wetting characteristic to the vessel when compared to the glue, to inhibit the glue from penetrating into the inner surface of lumen.

When the clamps 7 and 8 are removed (FIG. 5), the stimuli such as heat which was being applied to maintain the gel in a solid state is removed and gel changes phase to a liquid. Once the gel reverses its phase change to become a liquid and the blood flow against the liquefying gel causes the gel to be dispersed, the vessel reopen as shown in FIG. 6.

In the case where waxes are employed, heat can be applied to the joined lumens to melt the wax. Moreover, if the clamps are removed prior to application of heat, both melting and dissolution of the wax into the body fluid can occur.

In the case where thixotropic agents are employed, the application of shear stress to the mass, such as gentle squeezing of the joined lumens or the stress arising from the pumping action of the heart, will significantly reduce the viscosity of the mass and render it flowable with the body fluid.

Figure 5:
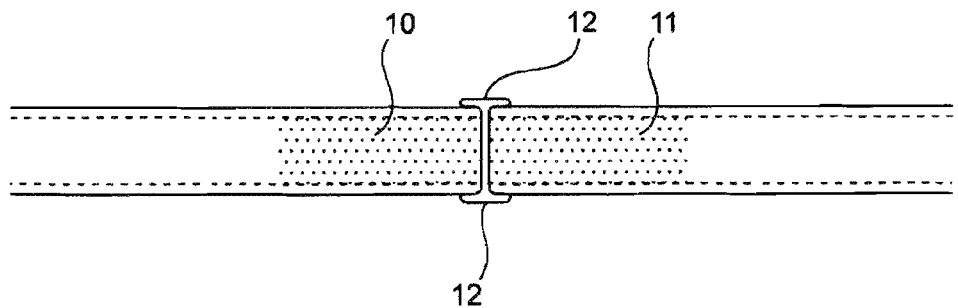
FIG. 5 is a schematic cross-sectional view of the tubular tissue of FIG. 1 with the ends sealed, the sol-gel (reversed to liquid phase) in place and the clamps removed.
Figure 6:
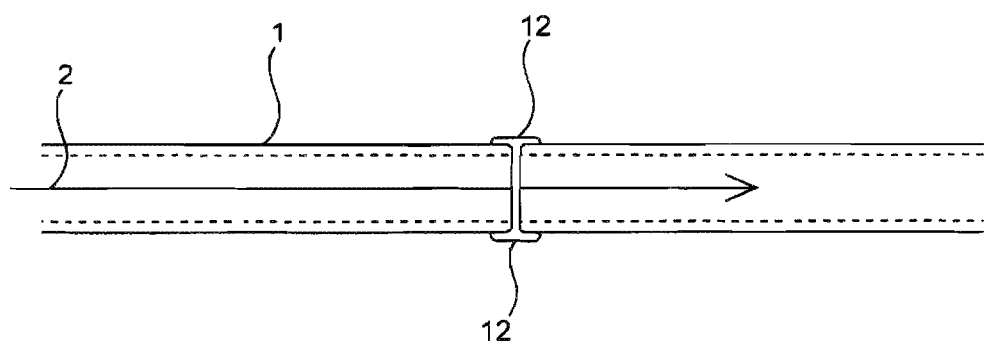
FIG. 6 is a cross-sectional view of the tubular tissue of FIG. 1 showing the sol-gel dissolved and flow restored with the blockage area removed.

At this point as shown in FIG. 5, the glue 12 has cured or hardened. The glue 12 seals the ends of the vessels together but also is applied to the outer surface of the vessel on either side of the point of connection where it is circumferentially applied. Accordingly, when the glue 12 hardens the glue 12 acts as an external stent holding the vessel 1 open after the gel has liquefied. Although it is not necessary to have the glue forming the external stent, this can provide an additional advantage. The glue may be designed so that it remains in place for a considerable period of time or designed so that it dissolves slowly over time as the two ends of the vessel grow together.

Those skilled in the art will understand that particularly high temperatures will not be useful for treating a patient as this may cause undue heat damage to live tissues. A transition temperature of around 42° C. to maintain the gel in the solid state might be used provided the gel will revert to its liquid state at around body temperature or 37° C. In this particularly described embodiment, temperature is used as the mechanism for causing the gel to undergo a phase change. However, as indicated above, other factors such as pH, ion concentration such as calcium ion concentration and the like can be used. Regardless of the particular parameter used to undergo the phase transition, the formulation will take into consideration factors such as the normal temperature, normal pH, normal ion concentration of the subject being operated on. In one embodiment, the gel will be in a liquid phase when the parameter such as temperature, pH or calcium ion concentration is at or very close to that of the surrounding environment and will be in a solid or gel phase when it is raised somewhat above or below the normal point but not sufficiently far from normal so as to be damaging to the tissue. Thus, high temperatures, extremely high or low pHs, as well as very high or low ion concentrations, would not be used, as such would likely cause damage to the surrounding tissue.

It has been demonstrated in mammalian experiments, that by performing an anastomosis procedure using the method and composition of the present invention, the time required to connect the blood vessels is significantly reduced to an average of 3 minutes 11 seconds (ranging from 55 seconds to 6 minutes), from an average of 29 minutes 15 seconds (ranging from 20 to 49 minutes) with conventional hand-sewn anastomosis procedures. See Example 1. This in turn resulted in improved outcomes of the procedures in terms of the diameters and patency rates of the vessels connected, complications caused by the procedures and the mortality rates of the subjects treated. See Example 1. Further, the experiments showed that anastomotic flow and burst strength at six weeks after the anastomosis procedures using the present invention were about the same if not better than using conventional hand-sewn procedures.

It is contemplated that the methods of the present invention are useful in other medical procedures, such as reversal of vasectomy, reversal of fallopian tube ligation, and reconstructive tubal surgeries to treat blocked or damaged fallopian tubes. The method can also be used to connect an AV graft or AV shunt to a blood vessel for hemodialysis. Further the method of the present invention can be used in alimentary anastomosis. Significant leak rates (about 2-5%) have been resulted by current alimentary anastomosis procedures. Many of the leak incidents are fatal or lead to significant morbidity. Because the alimentary tubes being ligated can be supported inside by the sol-gel of the present invention and the glue can be applied circumferentially outside the point of connection, thus allowing complete sealing, it is contemplated that anastomosis using the method of the present invention will significantly reduce the leak rate and lead to decreased mortality and morbidity caused by alimentary anastomosis. The methods and compositions of the present invention can also be used in the treatment of conditions involving urinary tracts, tear ducts, bowel, mammary ducts, pancreatic ducts, bile ducts, and the like.

IV. Kits of the Invention

One aspect of this invention is in the form of a kit of parts. The kit may include specific instructions with respect to how to carry out the methodology of the invention as exemplified above.

Further, the kit may include a container containing the solid mass or solid mass precursor e.g., the solution phase of a sol-gel composition, preferably in sterile form, and a delivery device. The delivery device may be a syringe or a pipette or tweezers and the like. Alternatively, the kit may contain a delivery device loaded with a flowable form of the solid mass material of the type described above, again preferably in sterile form. For example, the kit may contain a syringe already loaded with a sterile sol-gel composition or an ampule made from glass or plastic that contains a sterile sol-gel composition, and which has a tip that may be cut open to apply the sol-gel contained therein.

When a solid mass material is provided in the kit, it can be in a rod form of defined diameter so as to match the diameter of the lumen to which the solid mass is to be inserted.

Still further, the kit may include one, two or more clamps of the type which might generally be used in connection with the lumen or type of vessel (or duct, tube, etc.) being treated. Still further, the kit may include sutures or surgical glue of the type described above. Still further, the kit may include a component which, when activated, results in phase transition of the sol-gel material. For example, the component may be a component which when activated generates heat or when activated generates cold which can be used to maintain the sol-gel in its solid or gel like phase until it is removed. Such component may be a heating element, such as a heated air blower capable of delivering warm air at a temperature sufficient to induce the change of phase of the thermoreversible sol-gel.

The kit may further include one or more pharmaceutically active drugs which may be separate from or incorporated into the solid mass or its liquid precursor. Thus, for example, the drug which may be provided separately in the kit or incorporated into the solid mass or its liquid precursor may include an anticoagulant such as heparin. The solid mass or its liquid precursor may further include an antibiotic or other material such as a wound healing medicament which aids in healing of the vessel.

Commercially, for ease in practical application, materials may be prepared so that they are sterile and substantially pyrogen free, for example, in accordance with regulatory requirements. Materials and devices may be prepackaged in sterile packaging.

V. EXAMPLES

Examples 1-3 are working examples demonstrating the practicability of the present invention. Example 1 demonstrates that, for a thermoreversible composition, gelation temperature may be optimized by the addition of an additional moiety. Example 2 demonstrates the practicability of the present invention in an anastomosis animal model, demonstrating improved results over traditional methods in terms of increased body fluid flow and decreased mortality, in preliminary results. Example 3 demonstrates the additional aspect of use of the present methods and compositions for sustained delivery of a biologically active molecule, here, heparin, the blood thinner. Examples 4-6 are prophetic examples of practicability in human anastomosis procedures.

Example 1

Changing the Sol-Gel Transition Temperature of a Thermoreversible Sol-Gel Composition with the Addition of a Protein One embodiment of the present invention relates to exploitation of the sol-gel transition temperature of thermoreversible sol-gel compositions, and this working example demonstrates how the gelation temperature may be altered to be slightly above the normal body temperature. Therefore, this example allows a sol-gel material to assume a gel state inside the distal portion of the lumen when the temperature is temporally raised to above the transition temperature so that the geometry of the distal portion of the lumen is stabilized during the anastomosis procedure. After the anastomosis procedure, the temperature is returned to normal body temperature, which is below the transition temperature of the sol-gel material, so that the sol-gel material liquefies and becomes flowable in the conjoined lumen. This working example demonstrates that with an appropriate concentration of a protein, here bovine serum albumin, the gel-transition temperature of a thermoreversible sol-gel can be modulated to be slightly above the normal body temperature.

Figure 7:
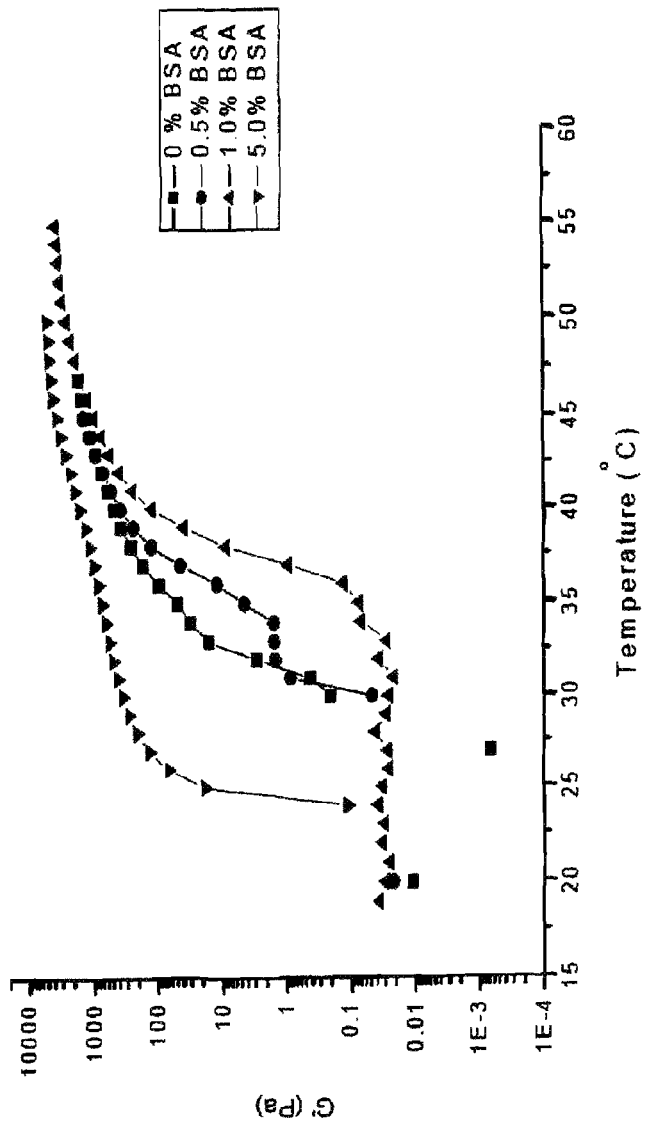
FIG. 7 is a graph of a triblock polymer versus temperature with no protein and three different concentrations of protein added.

A thermoreversible sol-gel which can be used in connection with the present invention is sold under the tradename Poloxamer 407®. The various pharmaceutical and pharmacological characteristics of Poloxamer 407® are described within Dumortier, Pharmaceutical Research, Vol. 23, No. 12, December 2006. Poloxamer 407® is a water soluble block copolymer comprised of poly(ethylene oxide) and poly(propylene oxide). The block polymer component is brought into solution in water. A graph of the modulus of the Poloxamer 407® in water (no BSA) over time is shown in FIG. 7 by the line graph with the rectangular data points. FIG. 7 shows that Poloaxmer 407® undergoes a phase transition between about 25° C. and about 30° C. where the modulus or stiffness of the polymer substantially increases forming the gel.

In accordance with the present invention it is beneficial to modify the sol-gel composition, such as a Poloxamer 407® solution, so as to shift the point at which the composition undergoes a phase change to a higher temperature. Although this can be accomplished by changing the concentration of the polymer in water, if this route is taken it tends to decrease the resulting modulus of the polymer gel formed.

Decreasing the modulus, or elastic modulus (G'), is not desirable for use in connection with the present invention. The compositions useful for this invention should have modulus that is sufficiently high to withstand the pressure applied on the outside of the vessels and to keep the vessels open when the vessels are manipulated during the anastomosis procedure. It is contemplated that the gels of the present invention shall have elastic modulus (G') values of from about 100 to about 500,000 Pascals, and preferably from about 100 to about 10,000 Pascals, and more preferably from about 150 to about 1500 Pascals.

Accordingly, it has been contemplated that by the inclusion of another molecule it might be possible to shift the phase transition point in terms of increasing the temperature at which the phase change takes place without decreasing the resulting modulus of the gel formed. It has been found here that by including a transition condition modulating agent which is biocompatible, such as a protein, it is possible to shift the temperature point at which the composition undergoes a phase change.

The data shown in FIG. 7 indicate that Bovine Serum Albumin (BSA) has been added first in a concentration of about 0.5% and then a concentration of about 1.0% and then a concentration of about 5%. The results shown in FIG. 7 indicate that by including the BSA in a composition in an amount of about 1% the phase transition point is shifted so that it occurs at about body temperature or at about 37.5° C.

The resulting composition with about 1% BSA provides a phase transition material which is biocompatible and provides a desirable transition temperature which has been varied without significantly changing the modulus of the resulting gel as compared to the gel without the added BSA.

A preferred formulation is comprised of about 17% polymer such as Poloxamer 407®, about 1% biocompatible compound such as BSA and about 82% water. Those skilled in the art will understand that each of these components can be varied in an amount of about ±50%, about =25%, about ±10%, about ±1% and, depending on the particular polymers and biocompatible compounds used, desirable results may be obtained.

In some embodiments, the biocompatible polymer may have a molecular weight in the range of about 8,000 to 16,000, more preferably 10,000 to 16,000, or more preferably 10,000 to 14,000 and most preferably about 12,600. (As indicated above, the term "about" as used in this context reflects that commercial preparations of the monomers or polymers as described herein may contain mixtures of varying molecular weights incident to the commercial manufacturing process.) That polymer is combined with a biocompatible compound which may be a protein and preferably a protein which does not elicit an immune response. The protein may be a blood protein such as an albumin and specifically may be Bovine Serum Albumin or Human Serum Albumin. (Also as indicated above, recombinant versions of such proteins (or any proteins as described herein) may be preferred for commercial manufacturing reasons, for assurance of no animal-originating pathogenic agents)

The polymer is present in the composition in an amount of about 15% to 20% by weight, or 16% to 18% by weight or 17% by weight. The polymer is combined with the biocompatible molecule in an amount of about 0.5% to 2% by weight or about 1% by weight. The remainder of the composition is water. The resulting composition is further characterized by undergoing a phase transition at a temperature higher than the phase transition temperature when the biocompatible compound is not present with a change in modulus of 25% or less, or 10% or less, or 5% or less. More particularly the resulting composition undergoes a phase transition in a relatively narrow range of about 35° C. to about 40° C. or about 36° C. to about 39° C. or more preferably about 37.5° C.

Those skilled in the art will be able to contemplate other phase transition materials which could be used in connection with the invention upon reading this disclosure and examining the data provided. The phase transition may be brought about by a change in condition other than temperature such as a change in pH and those skilled in the art will understand that that pH change may be a change which is brought about at a pH very close to the pH of human blood or a pH of about 7.2.

Presented here is a protocol for a 17% Polaxomer® 407 with 1% BSA. One of skill in the art may use different concentrations of the thermoreversable material or the protein.

The following materials were mixed together to form 100 ml (100 g) solution of 17% Polaxomer® 407 with 1% BSA:
   Phosphate buffered saline ("PBS"): 92 g, Gibco #10010, pH 7.4, with $Ca^{2+}$ and $Mg^{2+}$;
   Bovine Serum Albumin ("BSA"): 1 g, Sigma A2153-50 g;
   Polaxomer® 407: 17 g Poloxamer 407, BASF Pluronic® F 127 NF Prill Poloxamer 407, Material 30085239;
   Solutions having 17% Polaxomer® 407 and 0.1% BSA or 5% BSA were prepared accordingly.

To determine the sol-gel transition temperature (the temperature at which the Poloxamer 407 transitions from liquid to gel amounts of each solution were placed between the parallel plates of a stress rheometer (a TA Instruments G2 rheometer was used). The plates were 1 cm in diameter and the gap was set to 1 mm. The elastic modulus was measured using the rheometer at a frequency of 1 Hz and a strain of 0.1 at different temperatures. FIG. 7 is a graph depicting the modulus as a function of temperature. For BSA concentrations at or below 1%, the gelation temperature increased. The gel transition temperature, markedly decreased as the BSA concentration grew from 1% to 5%.

Example 2

Efficacy and Safety in an Animal Model Using Thermoreversible Anastomosis Compositions This working example demonstrates that the present anastomosis compositions are efficacious in joining tubular tissues to result in bodily fluid flow through the resultant continuous lumen.

Anastomosis Using Thermoreversible Gel

Anastomosis were performed in normal rats. The Poloxamer solution in this example refers to the thermoreversible composition containing 17% Polaxomer® 407 and 1% BSA, as prepared in Example 1, above. All animals are treated and cared for in accordance with all applicable laws and regulations, and in accordance with good laboratory practices.

End to End Anastomosis Surgical Method Performed on Cardiac Tubular Tissues in Rats:

Rats were anesthetized with isoflurane and prepped in sterile fashion with 70% ethanol. The aorta was exposed and isolated with blunt and sharp dissection through a midline laparotomy incision. The aorta was clamped proximally and distally, and subsequently divided and flushed with heparinized saline. In some cases the rat and poloxamer solution were warmed to 40° C. with sterile water, and then the poloxamer solution was injected in a semi-solid state and in other cases the polaxamer solution was injected into the vessels as a liquid and then heated to 40° C. with a convection source to solidify it. After direct reapproximation by pushing the ends of the aorta together, the cyanoacrylate adhesive was applied and allowed to cure for 60-120 seconds. The clamps were then removed, and the midline incision was closed in layers with 5-0 vicryl (Ethicon, Inc., Somerset, N.J.) and 4-0 nylon (Ethicon) in a running fashion.

End to Side Anastomosis Surgical Method:

Rats were anesthesized, shaved, and prepped in standard sterile fashion. A midline laparotomy incision was made and the abdominal organs eviscerated into a moist 4×4 gauze. The iliac bifurcation was isolated with blunt dissection, and the abdominal aorta was clamped proximally and the iliacs were clamped distally. The left iliac was divided just distal to the bifurcation and an arteriotomy was made in the right iliac. The vessels were then flushed with heparinized saline. The abdomen was warmed at the same time the poloxamer solution was warmed to a gel (about 40° C.) which was then injected. The left iliac was approximated to the right iliac using the sliding clamps (one clamp was on the proximal aorta and the other was on the distal left iliac). Once the ends were opposed without tension, the cyanoacrylate was applied and allowed to set (~5 min). Clamps were then removed and blood flow is restored.

Conventional Handsewn Anastomosis:

Rats were anesthesized, shaved, and prepped in standard sterile fashion. A midline laparotomy incision was made and abdominal organs were eviscerated. The aorta was isolated with blunt dissection and clamped proximally and distally and then divided. The two vessel ends were flushed with heparinized saline. The anastomosis was performed with a running 10-0 nylon suture. Each suture was full thickness through all layers of the aorta. Any areas of leakage were controlled with a simple interrupted suture, and the clamps were removed.

For the end-to-side anastomosis, the iliac bifurcation was isolated as previously described and clamped proximally and distally. The left iliac artery was divided near its origin and reapproximated to the right iliac artery using the clamps. An arteriotomy was made in the right iliac artery and both ends ware flushed with heparinized saline. The anastomosis was then performed with a running 10-0 nylon suture using standard microsurgical techniques and all areas of leakage were controlled with a simple interrupted suture. No successful end-to-side anastomosis were completed with the hand sewn technique.

Results

To evaluate the effectiveness of anastomosis using thermoreversible gel, the patency, flow and burst strength of the vessels connected were measured. The diameters of the anastomotic vessels were measured using conventional CT angiography. Patency and flow were determined through ultrasonic Doppler imaging using a visual sonic machine.

Burst Strength were Determined According to the Following Procedure:

Rats were anesthesized and native rat aortas were harvested prior to the operation and operated rat aortas at designated time points postoperatively through a midline laparotomy incision. The aorta was clamped proximally just below the renal arteries and just above the iliac bifurcation. Any small branches were identified and ligated. The harvested aorta was then flushed with saline to remove blood and identify any non-ligated branches. The aorta was then attached to a 22 gauge angiocath using 5-0 silk suture at both ends. The angiocath was equipped with an adapter than attaches directly to the burst strength device. Saline was flushed through the machine and through the aorta at calibrated pressures which were increased incrementally until the anastomosis burst.

Table 1 shows the anastomotic diameters, anastomotic flow, and burst strength of end-to-end anastomotic vessels connected using the thermoreversible sol-gel composition or by handsewing at six weeks post-operation. Patency and survival rate of end-to-end or end-to-side anastomosis using the two methods are compared in Tables 2 and 3.

TABLE 1

End-to-End Anastomosis results*

|  | Time per anastomosis | Anastomotic Diameter | Anastomotic Flow | Burst Strength |
| --- | --- | --- | --- | --- |
| TRGA group** | Average: 3 min. 11 sec. Range: 55 sec. to 6 min. | 1.93 mm (SD +/− .23 mm) | 75 ml/min (SD +/− 34 ml) | 1345 mmHg (SD +/− 190 mm) |
| handsewn group | Average: 29 min. 15 sec. Range: 20 to 49 min. | 1.23 mm (SD +/− .43 mm) | 63 ml/min (SD +/− 29 ml) | 1248 mmHg (SD +/− 206 mm) |
| p-value |  | 0.027 | not significant | not significant |

*preliminary results at six weeks
**Thermoreversible gel anastomosis group

TABLE 2

End-to-End Anastomosis results*

| Procedure used | Number of rats | Patency Rate among survivors | Number and causes of deaths |
| --- | --- | --- | --- |
| TRGA | n = 26 | 100% | One early anesthetic death. |
| Hand-sewn | n = 25 | 86% | Three early deaths from perioperative leak and hemorrhage; Two late deaths; Two distal ischemic events requiring sacrifice. |

TABLE 3

Side-to-End Anastomosis results*

| Procedure used | Number of rats | Patency Rate among survivors | Number and causes of deaths |
| --- | --- | --- | --- |
| TRGA | n = 13 | 100% | No deaths or ischemic events. |
| Hand-sewn | n = 10 | 10% | 60% with significant limb ischemia requiring sacrifice; One patent anastomosis occluded ipsilateral iliac at "toe". |

Example 3

Figure 8:
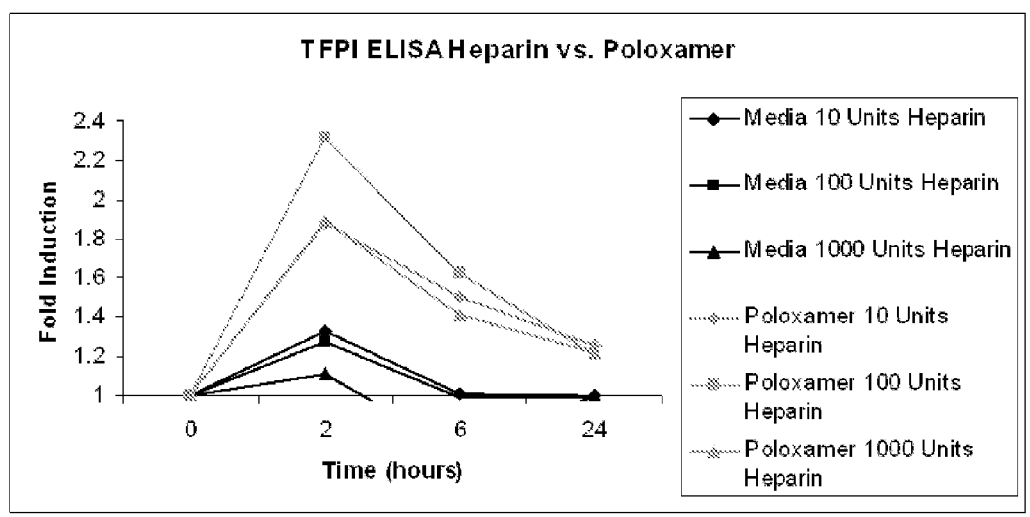
FIG. 8 is a graph of the effect of heparin delivered with poloxamer as compared with heparin delivered directly.

Use of Reversible Gel-Sol Anastomosis Compositions for Sustained Delivery of a Biologically Functional Molecule The present materials were used for delivery of heparin, as determined by an enzyme linked immunoadsorbent assay. The present thermoreversible sol-gel composition containing heparin was compared to media alone. Human umbilical vein endothelial cells were incubation for 5 minutes in trans-well plates. Heparin in varied concentrations (10, 100 and 1000 U/mL) were added to the cells directly or with poloximer. Tissue Factor Pathway Inhibitor (TFPI), tissue factor (TF), thrombomodulin (TM) were measured at 2 hr, 6 hr and 24 hr post heprin addition using a ELISA kit (R&D Systems, MN USA). As shown in FIG. 8, poloxamer-mediated delivery of heparin is more effective than direct administration of heparin. Further, the effects of heparin persist up to 24 hours with poloxamer mediated delivery, longer than with direct administration. This demonstrates that as the composition transitions from gel to liquid, the heparin is released for a sustained release effect.

The following Examples 4-6 are prophetic and have not yet been conducted. Rather these examples define methods which are readily correlated from Examples 1-3 above which were actually performed.

Example 4

Prophetic Example of Use of Wax Compositions in an Anastomosis Procedure

This prophetic example illustrates the use of a wax composition as the solid mass to provide structural support for a lumen during anastomosis. It is contemplated that the treated mammal will be anesthetized with isoflurane and prepped in sterile fashion with 70% ethanol. The aorta is exposed and clamped proximally and distally, and subsequently divided and flushed with heparinized saline. After being cut and flushed with saline, the temperature of the divided aorta becomes slightly lower than that of the body temperature. A wax composition having a melting point at about the normal rat body temperature, for example, a mixture of capric acid and lauric acid, is placed in the two open ends of the divided aorta in a matter to maintain the structural integrity of the aorta. After direct reapproximation by pushing the ends of the aorta together, the cyanoacrylate adhesive is applied and allowed to cure for 60-120 seconds. The clamps are then removed to allow blood to flow to the anastomosis point, causing the temperature to rise to about body temperature, which is sufficient to melt the wax composition and establish blood flow through the entire aorta.

In another example, a wax composition having a melting point slightly higher than the body temperature is preformed into a "stick" configuration of a diameter similar to that of the above aorta. The stick is inserted to one end of the aorta in a manner that a portion of the stick protrudes outside the aorta. The protruding portion of the stick is then inserted into the other end of the aorta so that the two ends are brought together. The cyanoacrylate adhesive is applied and allowed to cure for 60-120 seconds. The anastomosis point is warmed up to the melting point of the wax to melt the wax stick inside the aorta. The clamps are then removed to allow blood flow to be restored.

Example 5

Prophetic Example of Use of Thermoreversible Sol-Gel Compositions for a Vavovasectomy This prophetic example illustrates how the present invention could be used to connect tubular tissues which do not need immediate restoration of body fluid flow, but rather may benefit from a gradual healing, and therefore, a slower degradation of the subject sol-gel material in situ. A patient desires a vavovasectomy to reverse a vasectomy. The practitioner locates the previously cut vas deferens termini, and re-cuts a portion to open the tubular tissue lumen. A sol-gel composition of pasty texture is placed into the termini of each portion of the vas deferens, thereby stabilizing the tubular geometry. The stabilized termini are matched up, and methacrylate or other bio adhesive is applied and allowed to cure, if appropriate. The sol-gel composition does not immediately liquefy, but gradually biodegrades into constituent moieties which are absorbed by the surrounding tissue. The sol-gel optionally locally delivers in a sustained release fashion wound healing or anti-inflammatory biologically functional moieties, so that the now-reattached vas deferens does not occlude or become re-blocked due to scar tissue or undue inflammatory response.

The procedure described above may be used in other surgical procedures to remove blockage of other tubular tissues. It is contemplated that a dye may be incorporated into the wax composition for easy alignment of the non-conjoined lumens, especially for a lumen having a thick wall where the lumen is difficult to see.

Example 6

Prophetic Example of Use of Sol-Gel Material and Adhesive Ligation

This prophetic example illustrates an example of initiation of anastomosis using a photoinitiation solidification and an enzymatically-initiated liquefication using a sol-gel composition engineered to have photoactivatable cross-linking initiation sites, and enzyme-recognitions site for biodegradation. The sol-gel transitions toward solid upon exposure to the appropriate wavelength of light, and transitions toward liquid upon exposure to the enzyme, (or becomes more liquid) and dissolves into the systemic circulation, for example. A practitioner deploys the substantially liquid sol-gel to the terminus of a first tubular tissue, and applies a suitable wavelength of light for substantially solidifying the sol-gel. If the tubular tissue is in vivo, the light may be applied using fiber optic means, or if the tubular tissue is ex vivo, a suitable light source may be applied. The polymeric backbone of the sol-gel may be engineered to include an enzyme recognition site, such as a protease recognition site. The practitioner matches up the termini of the tubular tissue, and applies adhesive externally to the seam where the termini adjoin, and allows the sealant to cure, thereby creating a contiguous tubular tissue. Enzyme is injected into the location of the substantially solidified sol-gel and the sol-gel is digested into constituent parts, which are then absorbed by surrounding tissue or removed as part of the systemic body waste removal.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for joining at least two non-conjoined lumens in a patient which method comprises:
    a) placing a biocompatible sol-gel composition in a liquid phase or a gel phase in at least the distal portion of at least one of the lumens by injection with a hypodermic needle and/or a syringe, wherein when the sol-gel composition is placed in the lumen in the liquid phase, a phase transition is induced wherein the liquid phase changes to the gel phase, and wherein the gel phase of the sol-gel composition provides structural support to said portion of the lumen to facilitate joining of the lumens;
    b) aligning the lumens;
    c) closing the aligned lumens to form a conduit; and
    d) removing the sol-gel composition by inducing a phase transition of the sol-gel composition from the gel phase to the liquid phase thereby establishing flow through the conduit.

2. The method of claim 1, wherein the sol-gel composition is placed in the distal portion of each lumen to be joined.

3. The method of claim 1, wherein the sol-gel composition is placed in the distal portion of a first lumen in a manner in which the solid mass protrudes from the distal portion such that this protrusion can be used as a male mating functionality with the distal portion of the second lumen which acts as a female mating functionality.

4. The method of claim 1, wherein the sol-gel composition is sterile.

5. The method of claim 1, wherein the sol-gel composition is a phase-reversible sol-gel.

6. The method of claim 1, wherein the sol-gel composition further comprises a biologically active agent.

7. The method of claim 6, wherein the biologically active agent is selected from among one or more of: an antithrombotic moiety, an anti-anginal moiety, an anti-coagulant, an antiinfective, an analgesic, an antiinflammatory moiety, an antiarrhythmic moiety, an antihypertensive moiety, a heart failure agent, a wound healing agent, an antiasthmatic agent, an antidiuretic agent, an antineoplastic agent, an antipyretic agent, and antispasmodic agent, and anticholinergic agent, an immunosuppressive agent, a sympathomimetic agent, a central nervous system stimulant; a parasympatholytic agent, a parasympathomimetic agent, a hormone, a muscle relaxant, a lipid lowering agent; an anti-ulcer agent, an anorexic, an antiarthritic, an anticonvulsant; an antidepressant; a sedative; and a tranquilizer.

8. The method of claim 7, wherein the biologically active agent is an anti-coagulant.

9. The method of claim 8, wherein the anti-coagulant is heparin.

10. The method of claim 1, wherein the sol-gel composition further comprises one or both moieties selected from a biocompatible dye and a contrast agent.

11. The method of claim 1, wherein the sol-gel composition is a phase-reversible sol-gel having an elastic modulus (G') of at least about 100 to about 500,000 Pascals when in a gel phase.

12. The method of claim 11, wherein the elastic modulus (G') is from about 100 to about 20,000 Pascals.

13. The method of claim 1, wherein the sol-gel composition is a thermoreversible sol-gel.

14. The method of claim 13, wherein the thermoreversible sol-gel has a transition temperature of from about 35 ° C. to about 42 ° C.

15. The method of claim 13, wherein the phase transition of the thermoreversible sol-gel occurs due to a change in temperature of about ±1 ° C. to about ±10 ° C.

16. The method of claim 13, wherein the thermoreversible sol-gel comprises a polymer and a solvent.

17. The method of claim 16, wherein the solvent is water.

18. The method of claim 17, wherein the polymer is a copolymer of poly(ethylene oxide) and poly(propylene oxide).

19. The method of claim 18, wherein the copolymer has a molecular weight of from about 8,000 to about 16,000.

20. The method of claim 18, wherein the copolymer is present in an amount of about 15% to about 20% by weight.

21. The method of claim 18, wherein the thermoreversible sol-gel further comprises a protein.

22. The method of claim 21, wherein the copolymer is present in an amount of about 15% to about 20% by weight, the protein is present in an amount of about 0.5% to about 2.0% by weight.

23. The method of claim 21, wherein the copolymer is present in an amount of about 17% by weight ±20% of the 17%, the protein is present in an amount of about 1% by weight ±20% of the 1% and water in an amount of about 82% by weight ±20% of the 82%.

24. The method of claim 21, wherein said protein is an albumin.

25. The method of claim 24, wherein the albumin is selected from the group consisting of bovine serum albumin and human serum albumin.

26. The method of claim 1, wherein the first lumen is a vessel of the cardiovascular system of a human.

27. The method of claim 26, wherein the second lumen is selected from the group consisting of a vessel of the cardiovascular system of a human, an arteriovenous graft, an arteriovenous shunt, an allograft, a xenograft, and a synthetic graft.

28. The method of claim 27, wherein the second lumen is a cadaver xenograft.

29. The method of claim 1, wherein at least one of the lumens has a diameter of less than 1 mm.

30. The method of claim 1, wherein the two lumens are selected from the group consisting of human fallopian tubes, vasa deferentia, tubes in the alimentary canal, pancreatic ducts, bile ducts, tear ducts, and mammary ducts.

31. The method of claim 1, wherein joining of the lumens is conducted using a biocompatible adhesive or with sutures.

32. The method of claim 31, wherein the biocompatible adhesive is selected from among a cyanoacrylate-based adhesive, a fibrin-based adhesive, a polyurethane-based adhesive, and a polyisocyanate-based adhesive.

33. The method of claim 31, wherein the adhesive is applied to the cross-sectional surfaces of the lumens.

34. The method of claim 31, wherein the adhesive is applied around the circumference of the joined lumens.

35. The method of 34, wherein the adhesive further forms an external stent.

36. The method of claim 1, wherein the lumens are joined end to end.

37. The method of claim 1, wherein the lumens are joined end to side.

38. The method of claim 1, wherein the lumens are joined side to side.

39. A method for joining at least two non-conjoined lumens having distal ends, comprising the steps of:
   a) placing a phase-reversible sol-gel in a liquid phase inside at least a portion of the distal end of the first lumen by injection with a hypodermic needle and/or syringe, and inducing a phase transition wherein the liquid phase changes to a gel phase, and wherein the gel phase of the sol-gel composition provides structural support to said portion of the first lumen;
   b) placing a phase-reversible sol-gel in a liquid phase inside at least a portion of the distal end of a second lumen by injection with a hypodermic needle and/or a syringe, and inducing a phase transition wherein the liquid phase changes to a gel phase, and wherein the gel phase of the sol-gel composition provides structural support to said portion of the second lumen;
   c) aligning the distal portions of the first and second lumens;
   d) joining said lumens so as to provide for a conduit;
   e) inducing a phase change in the phase-reversible sol-gel in said conduit wherein said gel phase changes to a liquid phase; and
   f) allowing flow through said conduit.

40. A method for joining at least two non-conjoined lumens having distal ends, comprising the steps of:
   a) placing a phase-reversible sol-gel in a gel phase inside at least a portion of the distal end of a first lumen by injection with a hypodermic needle and/or a syringe, and in a manner which provides structural support to said portion of the first lumen;
   b) placing a phase-reversible sol-gel in a gel phase inside at least a portion of the distal end of a second lumen by injection with a hypodermic needle and/or a syringe, and in a manner which provides structural support to said portion of the second lumen;
   c) aligning the distal portions of the first and second lumens;
   d) joining said lumens so as to provide for a conduit;
   e) inducing a phase change in the phase-reversible sol-gel in said conduit wherein said gel phase changes to a liquid phase; and
   f) allowing flow through said conduit.

41. A method for joining at least two non-conjoined lumens having distal ends, comprising the steps of:
   a) placing a phase-reversible sol-gel in a liquid phase or a gel phase inside at least a portion of the distal end of a first lumen by injection with a hypodermic needle and/or a syringe, wherein when the sol-gel composition is placed in the lumen in the liquid phase, a phase transition is induced wherein the liquid phase changes to the gel phase, and wherein the gel phase of the sol-gel composition provides structural support to said portion of the first lumen and wherein said sol-gel protrudes from the distal end;
   b) mating the distal end of a second lumen with said protrusion from the first lumen thereby aligning the first and second lumens;
   c) joining said lumens so as to provide for a conduit;
   d) inducing a phase change in the phase-reversible sol-gel in said conduit wherein said gel phase changes to a liquid phase; and
   e) allowing flow through said conduit.

42. A method of connecting lumens within a living mammal, comprising the steps of:
   providing a phase-reversible gel inside a first lumen by injection with a hypodermic needle and/or syringe, and in a manner which holds the first lumen open;
   providing a phase-reversible gel inside a second lumen by injection with a hypodermic needle and and/or a syringe, and in a manner which holds the second lumen open;
   applying adhesive between an end of the first lumen and an end of the second lumen and allowing the adhesive to form bonds between the first and second lumens;
   inducing a phase change in the phase-reversible gel inside the first lumen and inside the second lumen; and
   allowing flow through the first lumen to the second lumen.

* * * * *